United States Patent [19]
Sherman et al.

[11] Patent Number: 5,707,861
[45] Date of Patent: Jan. 13, 1998

[54] DISINTEGRATOR OF LIVING CELLS

[75] Inventors: Michael Sherman, Newton; Yury Sherman; Katerina Sherman, both of Roslindale, all of Mass.

[73] Assignee: Scientific Industries, Inc., Bohemia, N.Y.

[21] Appl. No.: 528,115

[22] Filed: Sep. 14, 1995

[51] Int. Cl.⁶ .................................................. C12M 1/02
[52] U.S. Cl. .................. 435/306.1; 435/809; 422/104; 211/78; 241/170; 366/110
[58] Field of Search .................... 435/259, 283.1, 435/306.1, 809; 422/99, 102, 104; 211/70, 74, 77, 78, 163; 241/2, 170, 172, 175; 366/108, 110, 111, 112

[56] References Cited

U.S. PATENT DOCUMENTS

| | | | |
|---|---|---|---|
| 4,004,883 | 1/1977 | Meyer et al. | 422/104 |
| 4,202,634 | 5/1980 | Kraft et al. | 366/111 |
| 4,295,613 | 10/1981 | Moore et al. | 435/306.1 |
| 4,305,668 | 12/1981 | Bilbrey | 366/111 |
| 4,747,693 | 5/1988 | Kahl | 422/104 |
| 4,883,644 | 11/1989 | Perlman | 366/110 |

*Primary Examiner*—William H. Beisner
*Attorney, Agent, or Firm*—Ostrolenk, Faber, Gerb & Soffen, LLP

[57] ABSTRACT

An auxiliary holder of tubes intended for disintegration of living cells, such as yeast cells, in the presence of glass beads, as well as for mixing substances and pellet resuspension. The holder is installed on a vibrator. Due to specially-made gaps between the tubes and the main parts of the holder the processed cells and substances are subjected to a complex impact of vibration created by the vibrator and shocks created by the holder. The holder strongly enhances the effectiveness of the vibrator. During the disintegrating process the presence of a researcher is not required.

20 Claims, 2 Drawing Sheets

DISINTEGRATOR OF LIVING CELLS

BACKGROUND OF THE INVENTION

Vibrators are utilized for the disintegrating of cells, for example yeast cells, which are used in laboratory experiments. According to standard procedure, a small amount of a substance containing cells to be disintegrated is placed into a tube, for example an eppendorf tube, together with glass beads. Then the tubes are placed into a special attachment affixed to a vibrator and the cells are subjected to vibration. During the disintegrating procedure, which usually lasts 5 minutes or more, a researcher holds the tubes. During the procedure her/his hand is subjected to injurious and harsh vibrations. As a result, most researchers complain of pain and trembling in their hands. In many cases, as a requirement of the experiment, researchers have to work in a cold room.

Different types of tube holders are used for mixing substances and pellet resuspension. But existing holders are ineffective for disintegrating the cells, because their mass is not great enough to provide the required energy for cell vibration inside the tube.

SUMMARY OF THE INVENTION

Accordingly, it is the object of the present invention to provide for a tube holder which can be used for disintegrating cells, such as yeast cells, for example, in eppendorf tubes in the presence of glass beads. The holder can also be used for mixing substances and for pellet resuspension.

The holder consists of four main parts:

a shaft affixed to a vibrator mover;

a driving wheel affixed to the shaft, having a number of peripheral holes; the diameter of the holes being larger than the diameter of the tubes, so that there is a gap between the tubes and the driving wheel;

a shocking wheel having a central hole and a number of peripheral holes; the diameter of the central hole being larger than the diameter of the shaft, so that there is a gap between the shaft and the shocking wheel; the diameter of the peripheral holes of the shocking wheel being larger than the diameter of the tubes, so that there is a gap between the tubes and the shocking wheel; and a removable cap placed above the driving and shocking wheels, the cap preventing the tubes from flying out of the holder which as a result of a strong impact of vibration and shock to the tubes, where a gap is provided between the cap and the tubes;

Due to the gaps between the tubes and the parts of the holder the tubes are subjected to multiple shocks during vibration. These shocks strongly enhance the effectiveness of vibration.

The procedure does not require the presence of the researcher.

The holder can be also effectively used for mixing substances and pellet resuspension.

DESCRIPTION OF THE PREFERRED EMBODIMENT

Figure 1:
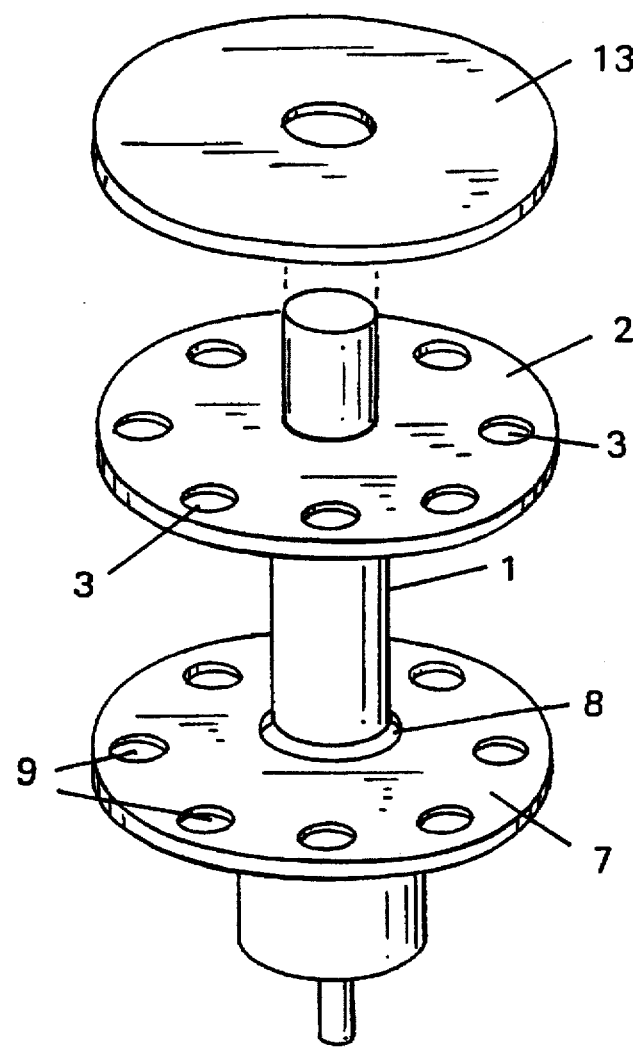
FIG. 1. is an isometric view of the holder.

Referring to the drawing in more detail, in FIG. 1 the invented holder in preferred embodiment is shown. The holder includes the shaft 1 which can be affixed to a vibrator by any convenient means.

Figure 2:
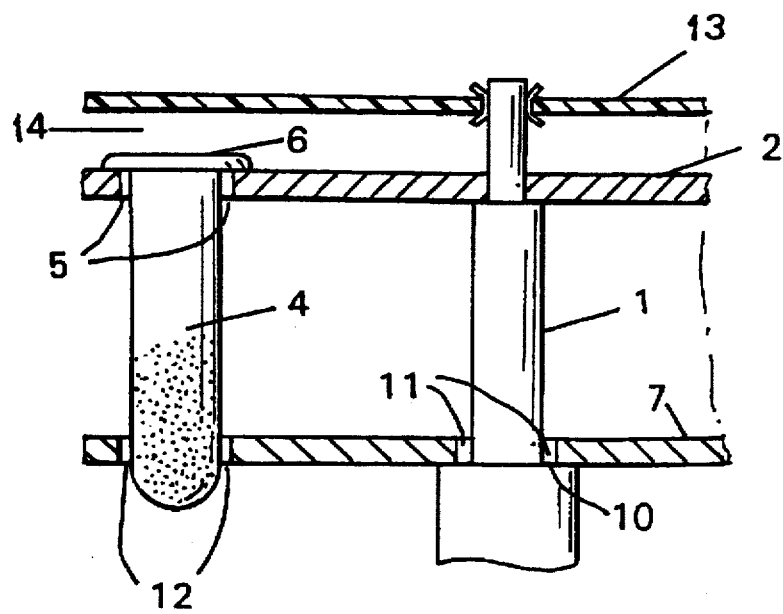
FIG. 2. is a fragment of the holder with the installed tube.

A driving wheel 2 is affixed to the shaft by any convenient means. The driving wheel 2 has a number of peripheral holes 3 that the tubes can pass through. As is shown in FIG. 2 the diameters of the holes 3 are larger than the diameter of the tubes 4, so that there are gaps 5 between the tubes and the driving wheel. However, the diameters of the holes 3 are smaller than the diameter of the tube flange 6, so that the tubes rest upon the driving wheel.

A shocking wheel 7 is located below the driving wheel at a distance of approximately 0.85 tube lengths therefrom. The shocking wheel has a central hole 8 and a number of peripheral holes 9. The shocking wheel rests upon a shoulder 10 of the shaft but is not affixed to the shaft. The diameter of the central hole 8 is larger than the diameter of the shaft 1, so that there is a gap 11 between the shaft and the shocking wheel. A central point in the central hole of the shocking wheel may or may not coincide with a central point of the shaft.

The diameters of the peripheral holes 9 are larger than the diameter of the tubes 4 where the tubes 4 pass through the holes 9, so that there are gap 12 between the tubes 4 and the shocking wheel 7.

A removable cap 13 is located above the driving wheel. The cap 13 prevents the tubes from flying out of the holder when the tubes are subjected to vibration and shocks. There is a gap 14 between the cap and the tubes.

For operation, the cap is removed and eppendorf tubes are positioned into the peripheral holes of the driving and shocking wheels. Then the cap is put on the shaft and the vibrator is switched on. After the disintegrating procedure is completed, all the operations should be preformed in reverse order.

Figure 3:
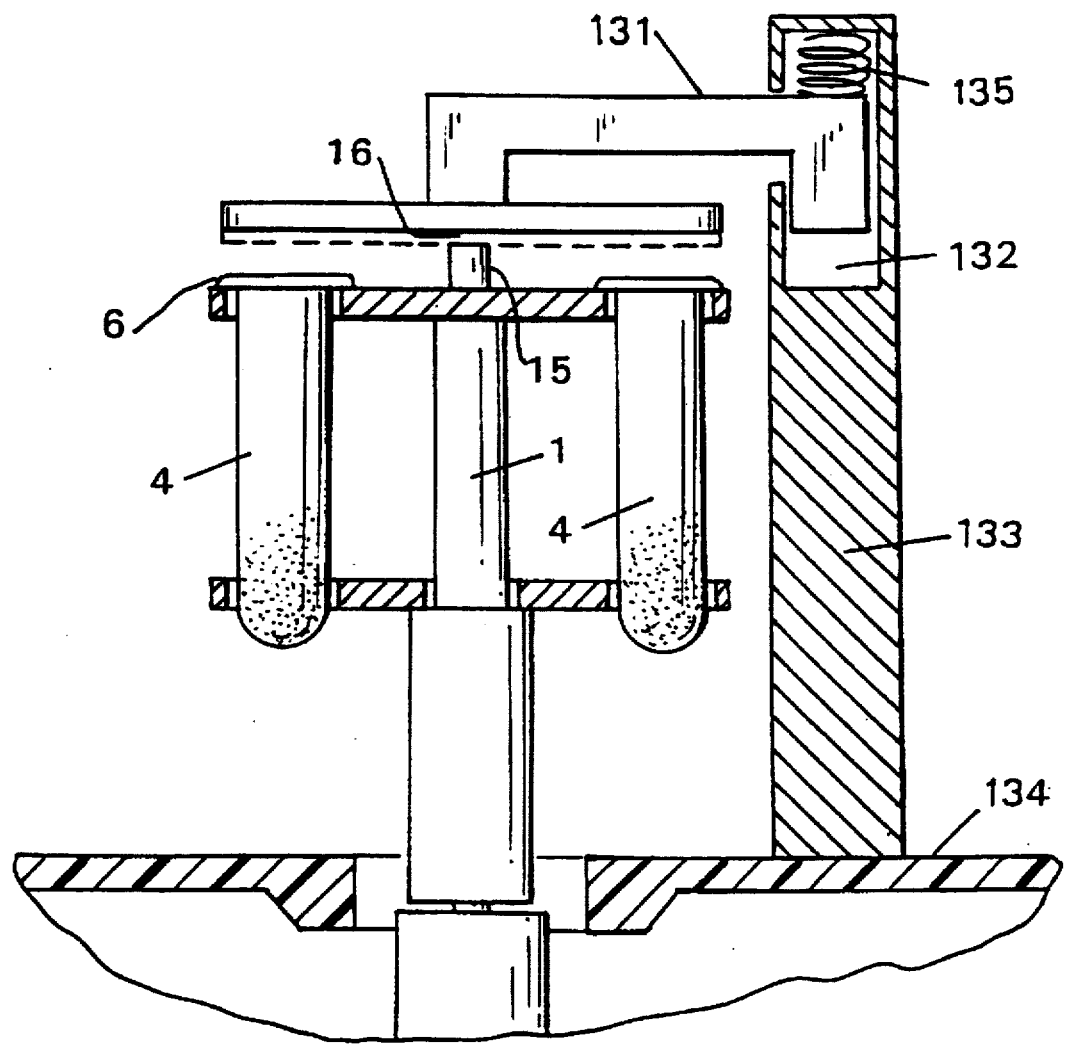
FIG. 3. is a cross-section of the holder in the second version.

Sometimes an axial vertical pressure on the vibrator mover is required for switching on the vibrator. Accordingly, the second version of the invention is shown in FIG. 3. In contrast to the first version the removable cap is replaced by a movable (up and down) cantilevered cap 131. The cap 131 slides inside the cavity 132 of a column 133 mounted outside the holder on the vibrator's housing 134. Between the column 133 and the cap 131 there is a spring means 135 which provides the required pressure of the cap 131 onto an extension 15 of the holder. In an inoperative position the cantilevered cap 131 is fixed to the column 133 so that there is a gap 16 between the cap 131 and the extension 15. In this position the spring means 135 is compressed For activating the vibrator, the cap 131 should be released. Under pressure of the spring means the cup 131 is biased downward and presses against the extension 15. The vibrator is then switched on.

This invention is not limited to the specific details shown since various modifications and structural changes are possible without departing in any way from the spirit of the present invention.

What is claimed is:

1. A tube holder for holding at least one tube, the holder comprising:

a shaft having means for coupling the shaft to a vibrator;

a driving member coupled to the shaft and including at least one first hole through which a first portion of the tube can pass, the hole being shaped such that the tube is engaged by the driving member at least while the driving member is vibrated by the shaft; and a shocking-member spaced from the driving member along the length of the tube shaped to be moveable with respect to the shaft, the shocking member including at least one second hole through which a second portion of the tube can pass, the second hole being larger in cross-section than the tube and sized so that as the tube is vibrated by the driving member, the tube may impact on the shocking member.

2. The tube holder of aim 1, wherein the first hole is sized larger in cross section than the first portion of the tube to produce a gap between the driving member and the first portion of the tube and the first hole is small enough in cross section that the driving member may vibrate the tube.

3. The tube holder of claim 2, wherein the first hole is smaller than a third support portion of the tube such that the support portion of the tube is supported by the driving member.

4. The tube holder of claim 2, wherein the shaft is shaped for supporting the shocking member spaced from the driving member.

5. The tube holder of claim 2, wherein the shocking member includes a mounting hole through which the shaft passes, and the mounting hole is larger in cross-section than the portion of the shaft which passes through the mounting hole producing a gap between the shaft and the shocking member such that the shocking member is movingly coupled with the shaft.

6. The tube holder of claim 5, wherein the shaft includes a shoulder thereon for supporting the shocking member spaced from the driving member.

7. The tube holder of claim 6, wherein the mounting hole is smaller in cross-section than the shoulder.

8. The tube holder of claim 7, wherein the center of the shaft is not coincident with the center of the mounting hole.

9. The tube holder of claim 5, wherein each of the driving member and the shocking member is in the shape of a respective disk, and each has a respective plurality of the first and second holes arranged in respective sets of a first and second hole for receiving a tube.

10. The tube holder of claim 9, wherein the pluralities of holes are disposed about the peripheries of the respective members.

11. The tube holder of claim 5, wherein the shocking member is spaced from the driving member approximately 0.85 of the length of the tube.

12. The tube holder of claim 1, further comprising a cap near the driving member for preventing the tube from disengaging from the driving member during vibration.

13. The tube holder of claim 12, wherein the cap is coupled to the shaft.

14. The tube holder of claim 13, wherein the cap is removable.

15. The tube holder of claim 12, further comprising a fixed column and a movable lever coupled to the column, the cap being coupled to the lever and biased against the shaft.

16. The tube holder of claim 15, further comprising a spring disposed in the column for biasing the lever and the cap toward the shaft.

17. A tube holder for a plurality of flanged tubes for disintegrating living cells, mixing substances, and pellet resuspension by vibration, comprising: a shaft, a driving wheel, and a shocking wheel;

the shaft having a shoulder; means for affixing the shaft to a vibrator;

the driving wheel being coupled to the shaft, the driving wheel having a plurality of peripheral holes the tubes can pass through, wherein the diameter of the peripheral holes is larger than the diameter of the tubes at the point the tubes pass through the holes, producing a gap between each tube and the driving wheel, the diameter of the peripheral holes of the driving wheel is less than the diameter of the flanges of the tubes, so that the tubes rest upon the driving wheel;

the shocking wheel resting upon the shoulder of the shaft a distance from the driving wheel which is less than the length of the tubes, the shocking wheel having a central hole the diameter of which is larger than the diameter of the shaft above the shoulder and less than the diameter of the shoulder, producing a gap between the shaft and the shocking wheel and so that the shocking wheel is free to move relative to the shaft, the shocking wheel having a plurality of peripheral holes which correspond to the holes of the driving wheel, wherein the diameter of the peripheral holes of the shocking wheel is larger than the diameter of the tubes at the point the tubes pass through the holes, producing a gap between each tube and the shocking wheel.

18. The tube holder of claim 17, including a removable cap positioned above the wheels for preventing the tubes from being displaced from the holder when subjected to vibrations and shocks.

19. The tube holder of claim 17, wherein the central point of the shaft does not coincide with the central point of the central hole of the shocking wheel.

20. The tube holder of claim 17, further including cantilever means for selectively providing vertical axial pressure on the shaft.

* * * * *